(12) United States Patent
Spenciner

(10) Patent No.: US 11,918,454 B2
(45) Date of Patent: *Mar. 5, 2024

(54) TISSUE FIXATION DEVICE

(71) Applicant: Medos International Sarl, Le Locle (CH)

(72) Inventor: David B. Spenciner, North Attleboro, MA (US)

(73) Assignee: Medos International Sarl, Le Locle (CH)

( * ) Notice: Subject to any disclaimer, the term of this patent is extended or adjusted under 35 U.S.C. 154(b) by 61 days.

This patent is subject to a terminal disclaimer.

(21) Appl. No.: 17/694,138

(22) Filed: Mar. 14, 2022

(65) Prior Publication Data

US 2022/0192816 A1    Jun. 23, 2022

Related U.S. Application Data

(60) Continuation of application No. 16/783,781, filed on Feb. 6, 2020, now Pat. No. 11,395,729, which is a
(Continued)

(51) Int. Cl.
*A61F 2/08* (2006.01)
*A61B 17/04* (2006.01)

(52) U.S. Cl.
CPC ............ *A61F 2/08* (2013.01); *A61B 17/0401* (2013.01); *A61F 2/0811* (2013.01);
(Continued)

(58) Field of Classification Search
CPC .. A61F 2/08; A61F 2/0811; A61F 2002/0823; A61F 2002/0829; A61F 2002/0852; A61F 2002/0882
See application file for complete search history.

(56) References Cited

U.S. PATENT DOCUMENTS 4,682,590 A    7/1987    Kothmann
5,306,301 A    4/1994    Graf et al.
(Continued)

FOREIGN PATENT DOCUMENTS

EP    1723917 A1    11/2006
EP    2777557 A1    9/2014
(Continued)

OTHER PUBLICATIONS

Extended European Search Report issued in European Application No. 17170888.6, dated Oct. 24, 2017, 8 pages.
(Continued)

*Primary Examiner* — Suba Ganesan

(57) ABSTRACT

Devices and methods for fixating a graft tendon in a bone tunnel for a ligament reconstruction or repair procedure are provided. In general, the described implantable tissue fixation device includes first and second elongate, substantially rigid support members that are discrete elements separated from each other, and at least one flexible member connecting the rigid support members. The tissue fixation device can have changeable dimensions such that it has at least one dimension that is smaller in a delivery configuration than in a deployed configuration. In both delivery and deployed configurations, the first and second rigid support members are positioned in a non-intersecting orientation with respect to one another. A graft retention loop coupled to the tissue fixation device has the graft tendon coupled thereto and extending into the bone tunnel so as affix the graft into the bone.

16 Claims, 9 Drawing Sheets

Related U.S. Application Data continuation of application No. 15/915,741, filed on Mar. 8, 2018, now Pat. No. 10,555,803, which is a division of application No. 14/730,484, filed on Jun. 4, 2015, now Pat. No. 9,937,032.

(52) U.S. Cl.
CPC .............. *A61F 2002/0823* (2013.01); *A61F 2002/0829* (2013.01); *A61F 2002/0852* (2013.01); *A61F 2002/0882* (2013.01)

(56) References Cited

U.S. PATENT DOCUMENTS

| | | | |
|---|---|---|---|
| 5,827,289 | A | 10/1998 | Reiley et al. |
| 6,127,597 | A | 10/2000 | Beyar et al. |
| 6,482,210 | B1 | 11/2002 | Skiba et al. |
| 6,860,901 | B1 | 3/2005 | Baker et al. |
| 7,494,496 | B2 | 2/2009 | Swain et al. |
| 7,500,983 | B1 | 3/2009 | Kaiser et al. |
| 8,491,632 | B2 | 7/2013 | Stone et al. |
| 8,834,524 | B2 | 9/2014 | Torrie et al. |
| 9,937,032 | B2 | 4/2018 | Spenciner |
| 10,085,830 | B2 | 10/2018 | Spenciner |
| 10,555,803 | B2 | 2/2020 | Spenciner |
| 2002/0082525 | A1 | 6/2002 | Oslund et al. |
| 2004/0073219 | A1* | 4/2004 | Skiba ................. A61F 2/0811 606/916 |
| 2004/0254609 | A1 | 12/2004 | Esplin |
| 2005/0277961 | A1* | 12/2005 | Stone ................ A61B 17/0401 606/151 |
| 2009/0204146 | A1 | 8/2009 | Kaiser et al. |
| 2009/0299327 | A1 | 12/2009 | Tilson et al. |
| 2010/0211075 | A1 | 8/2010 | Stone |
| 2010/0241214 | A1 | 9/2010 | Holzer et al. |
| 2010/0274355 | A1 | 10/2010 | McGuire et al. |
| 2012/0116402 | A1 | 5/2012 | Schneider |
| 2012/0290004 | A1 | 11/2012 | Lombardo et al. |
| 2012/0296345 | A1 | 11/2012 | Wack et al. |
| 2013/0123810 | A1 | 5/2013 | Brown et al. |
| 2014/0222148 | A1 | 8/2014 | Shinde |
| 2014/0243893 | A1 | 8/2014 | Santangelo et al. |
| 2015/0020410 | A1 | 1/2015 | Adesida |
| 2015/0025552 | A1 | 1/2015 | Stoll |
| 2015/0094742 | A1 | 4/2015 | Spenciner |
| 2020/0246130 | A1 | 8/2020 | Spenciner |

FOREIGN PATENT DOCUMENTS

| | | |
|---|---|---|
| FR | 2696338 A1 | 4/1994 |
| WO | 02065892 A2 | 8/2002 |
| WO | 2013054354 A2 | 4/2013 |

OTHER PUBLICATIONS

U.S. Appl. No. 14/730,484, filed Jun. 4, 2015, Tissue Fixation Device.

U.S. Appl. No. 15/915,741, filed Mar. 8, 2018, Tissue Fixation Device.

U.S. Appl. No. 16/783,781, filed Feb. 6, 2020, Tissue Fixation Device.

* cited by examiner

TISSUE FIXATION DEVICE

CROSS REFERENCE TO RELATED APPLICATION

The present application is a continuation of U.S. patent application Ser. No. 16/783,781, filed on Feb. 6, 2020, and entitled "TISSUE FIXATION DEVICE", which is a continuation of U.S. patent application Ser. No. 15/915,741, filed on Mar. 8, 2018, and entitled "TISSUE FIXATION DEVICE", now U.S. Pat. No. 10,555,803 issued on Feb. 11, 2020, which is a divisional of U.S. patent application Ser. No. 14/730,484, filed on Jun. 4, 2015, and entitled "TISSUE FIXATION DEVICE", now U.S. Pat. No. 9,937,032 issued on Apr. 10, 2018, each of which are hereby incorporated by reference in their entireties.

FIELD

Implantable tissue fixation devices as well as methods for using such tissue fixation devices are provided.

BACKGROUND

A ligament is a piece of fibrous tissue which connects one bone to another within the body. Ligaments are frequently damaged (e.g., detached, torn or ruptured) as the result of injury or accident. A damaged ligament can impede proper stability and motion of a joint and cause significant pain. A damaged ligament can be replaced or repaired using various procedures, a choice of which can depend on the particular ligament to be restored and on the extent of the damage. When ligaments are damaged, surgical reconstruction can be necessary, as the ligaments may not regenerate on their own.

An example of a ligament that is frequently damaged as a result of injury, overexertion, aging and/or accident is the anterior cruciate ligament (ACL) that extends between a top of the tibia and a bottom of the femur. Another ligament that is often damaged and may need to be replaced is a posterior cruciate ligament (PCL). A damaged ACL or PCL can cause instability of the knee joint, arthritis, and substantial pain.

ACL reconstruction or repair typically includes the use of a tendon graft replacement procedure which usually involves drilling a bone tunnel through the tibia and up into the femur. Then a graft, which may be an artificial ligament or harvested graft, such as a tendon, is passed through a tibial portion of the tunnel (sometimes referred to as "the tibial tunnel") across the interior of the joint, and up into a femoral portion of a tunnel (sometimes referred to as "the femoral tunnel"). One end of the ligament graft can then be secured in the femoral tunnel and another end of the graft is secured in the tibial tunnel, at the sites where the natural ligament attaches.

A number of conventional surgical procedures exist for re-attaching such ligament graft to bone, which have advantages and certain drawbacks. For example, a fixation device in the form of an elongate "button," sometimes referred to as a "cortical button" can be used for an ACL fixation to the femur. However, such devices are relatively wide, such that it is required to remove a substantial amount of bone in the femur to drill a tunnel sized sufficiently to receive the device therethrough. This can complicate the surgery and extend its duration, as well as to cause inconvenience to the patient and delay healing.

Accordingly, there is a need for improved tissue fixation devices and techniques for using such devices.

SUMMARY

An implantable tissue fixation device is provided that in some embodiments includes first and second elongate, substantially rigid support members that are discrete elements separated from each other. The implantable tissue fixation further includes at least one graft retention loop coupled to the tissue fixation device and at least one flexible member connecting the first and second rigid support members. The tissue fixation device can have changeable dimensions such that the device has a delivery configuration and a deployed configuration, wherein the tissue fixation device has at least one dimension that is smaller in the delivery configuration than in the deployed configuration, and wherein the first and second rigid support members are configured to be positioned in a non-intersecting orientation with respect to one another in the delivery configuration.

The tissue fixation device can vary in any number of ways. For example, in one aspect, the first and second rigid support members are configured to be positioned in a non-intersecting orientation with respect to one another in the delivery configuration.

In some embodiments, the tissue fixation device can include at least one third elongate, substantially rigid support member, and at least one second flexible member connecting the second and third rigid support members.

The at least one flexible member includes a fabric in one embodiment. In some embodiments, the at least one flexible member has a plurality of elongate connecting filaments extending between the rigid support members. The elongate connecting filaments can be formed from a same component. Further, the elongate connecting filaments can be suture or wire. In yet another embodiment, the at least one flexible member includes retaining channels each holding at least one of the rigid support members.

In one embodiment the rigid support members each include a plurality of retaining elements used to couple the plurality of elongate connecting filaments to the rigid support members. The plurality of retaining elements can include longitudinally spaced openings formed in the rigid support members.

In one embodiment, the at least one graft retention loop is coupled to the at least one flexible member and disposed around the rigid support members.

The tissue fixation device can further include at least one of first and second sutures removably coupled to opposite ends of the at least one flexible member, the first and second sutures extending at opposite directions along a length of the at least one flexible member.

In some aspects, a method for fixating a graft tendon into a bone tunnel is provided. The method includes forming a graft construct by coupling the graft tendon to a tissue fixation device via a graft retention loop of the tissue fixation device comprising first and at least one second elongate, substantially rigid support members that are discrete elements separated from each other and at least one flexible member connecting the rigid support members, passing the graft construct through the bone tunnel with the tissue fixation device in a delivery configuration such that the rigid support members are in a non-intersecting orientation relative to one another and are disposed a first distance away from one another, and, after the graft construct is passed up through the bone tunnel and is disposed over an opening in the bone tunnel, positioning the tissue fixation device over the opening in a deployed configuration such that the rigid support members are disposed a second distance away from one another that is greater than the first distance, and the graft retention loop and the graft tendon extend into the bone tunnel. The flexible member used in the method can be a fabric.

In one embodiment, the at least one flexible member includes a plurality of elongate connecting filaments extending between the rigid support members, and the elongate connecting filaments can be formed from a same component. The plurality of elongate connecting members include suture or metal wire. The rigid support members can each include a plurality of retaining elements used to couple the plurality of elongate connecting filaments to the rigid support members. The plurality of retaining elements include longitudinally spaced openings formed in the rigid support members. The at least one graft retention loop is coupled to the at least one flexible member and disposed around the rigid support members.

In another embodiment, the tissue fixation device further includes at least one suture removably coupled to an end of the at least one flexible member.

BRIEF DESCRIPTION OF THE DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings.

DETAILED DESCRIPTION

Figure 1A:
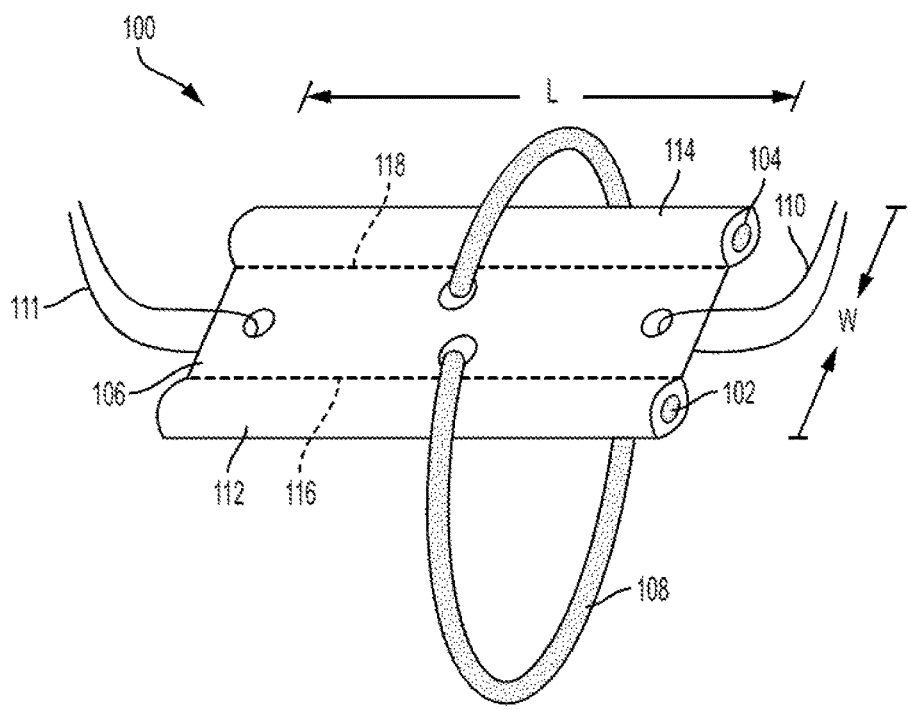
FIG. 1A is a perspective view of one embodiment of a tissue fixation device.

Certain exemplary embodiments will now be described to provide an overall understanding of the principles of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments and that the scope of the embodiments is defined solely by the claims. Further, the features illustrated or described in connection with one exemplary embodiment may be combined with the features of other embodiments. Such modifications and variations are intended to be included within the scope of the described embodiments.

The embodiments described herein generally relate to devices and methods for fixating tendon grafts during ligament reconstruction or augmentation surgeries. The implantable tissue fixation device can move between different configurations such that at least one of its dimensions can change. At the same time, the device has sufficient rigidity that allows it to withstand a load comparable to what larger devices could withstand.

The implantable tissue fixation device includes first and second elongate, substantially rigid support members separate from one another and at least one flexible member connecting the rigid support members. The tissue fixation device further includes at least one graft retention loop coupled to the tissue fixation device and configured to retain a tissue graft in place when the device is implanted. At least one dimension of the tissue fixation device can vary. Thus, in some embodiments, prior to or following the tissue fixation device being deployed, the rigid support members can be spaced apart at a distance that is equal or approximately equal to a width of the flexible member. The flexible member, which can be a single sheet or can be in the form of one or more filaments, can also be bent, rolled, folded, crimped, or otherwise manipulated so as to decrease a distance between the rigid support members. For example, the rigid support members can be brought closer together in a delivery configuration for passing the tissue fixation device through a bone tunnel to a point of fixation. In this way, a bone tunnel having a smaller diameter, as compared to a bone tunnel diameter required to pass a conventional device, can be formed.

In the delivery configuration, the rigid support members can be disposed in a non-intersecting orientation with respect to one another. The tissue fixation device is configured such that, after it is passed through the bone tunnel, it is positioned over an opening of the tunnel such that the rigid support members are similarly disposed in the non-intersecting orientation with respect to one another.

The devices and methods described herein provide a number of advantages over existing techniques for fixating tendon grafts. For example, as mentioned above, a bone tunnel of a reduced size can be formed, which requires removing less bone from the patient's body. This can decrease a possibility of complications at the surgical site and can ultimately decrease morbidity associated with the surgical procedure. In addition, because the overall tissue fixation device is more flexible and the rigid support members can move with respect to each other, the device can be positioned against bone such that to better conform to the curved surface of the bone. In this way, the tissue fixation device can be less palpable by the patient, as compared to existing devices. Furthermore, the described tissue fixation device is simplified and it can be more cost-effective.

The described devices and methods can be used in conjunction with a variety of tendon grafts, including hamstring tendon grafts, and in a variety of different surgical contexts regardless of the type of tendon graft being used in a particular surgical procedure. The devices and methods described herein can be utilized in connection with fixating grafts for repairing or replacing ligaments in a variety of joints. In some embodiments, the devices and methods described herein have particular utility in cruciate ligament reconstruction procedures. In some embodiments, the devices and methods described herein can be utilized for fixating tendon grafts for reconstruction procedures such as, for example, the cruciate ligaments of the knee.

Figure 1B:
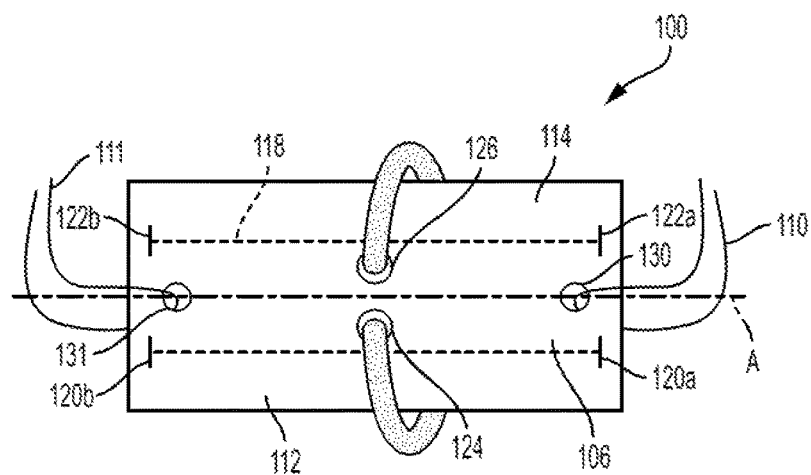
FIG. 1B is a top view of the tissue fixation device of FIG. 1A.
Figure 1C:
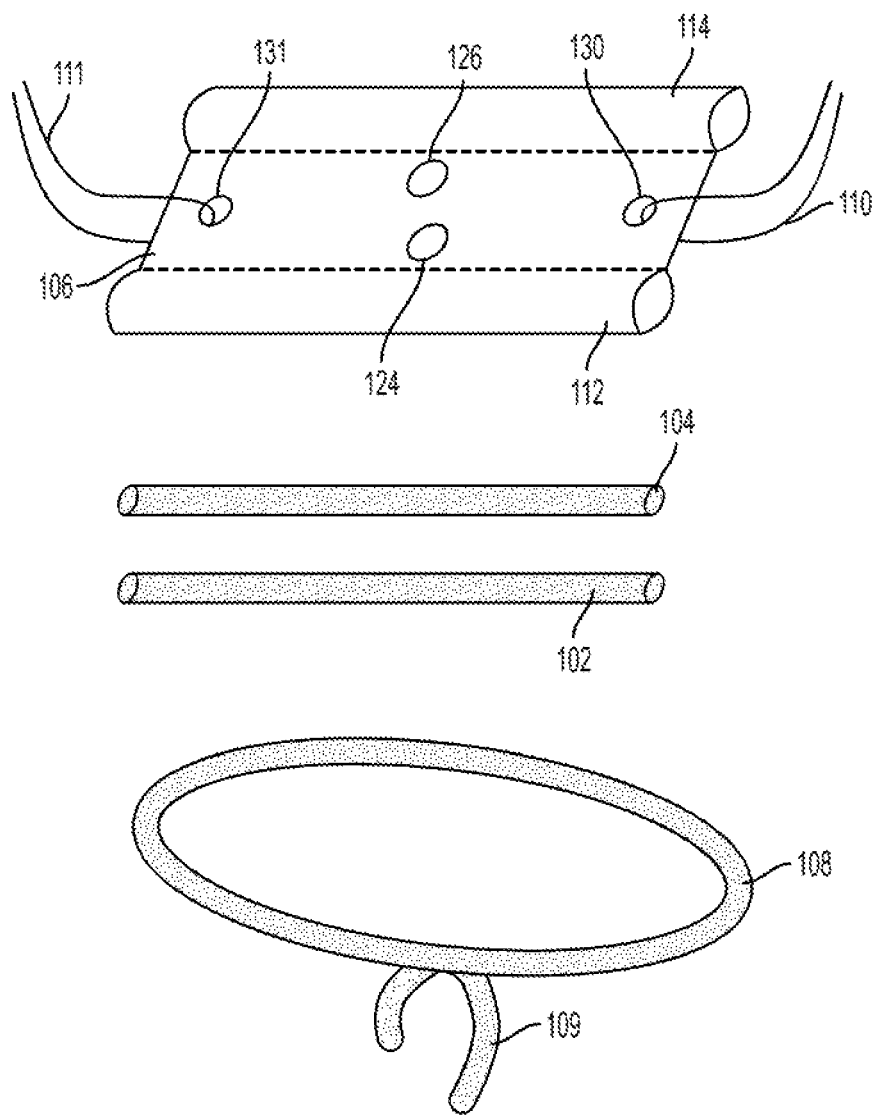
FIG. 1C is a exploded view of the tissue fixation device of FIG. 1A.

FIGS. 1A-1C illustrate one embodiment of an implantable tissue fixation device 100. The tissue fixation device 100 includes first and second substantially rigid elongate support members 102, 104, and at least one flexible member 106 connecting the first and second support members 102, 104. As shown, the tissue fixation device 100 also has at least one graft retention loop 108 coupled to the flexible member 106, as well as leading and trailing sutures 110, 111 also coupled to opposite ends of the flexible member 106. It should be appreciated that, in some embodiments, the tissue fixation device 100 can have one of the leading and trailing sutures 110, 111 rather than both the leading and trailing sutures 110, 111.

As shown in FIGS. 1A-1C, the tissue fixation device 100 in an original configuration (e.g., prior to delivery and deployment) can be generally rectangular. However, a person skilled in the art will appreciate that the tissue fixation device 100 can have any other shape. For example, in some embodiments, the tissue fixation device 100 can be square, circular or oval. The shape of the tissue fixation device 100 can be regular or irregular.

The tissue fixation device 100 has at least one changeable dimension such that the device 100 has a delivery configuration and a deployed configuration. The substantially rigid support members 102, 104 provide rigidity and structural support to the tissue fixation device 100, while the flexible member 106 is able to change its configuration to thereby allow the tissue fixation device 100 to adopt different configurations. Thus, at least one dimension (e.g., width) of the tissue fixation device 100 can be smaller in the delivery configuration than in the deployed configuration, as discussed in more detail below. Although the size of the tissue fixation device 100 in the delivery configuration, and, in some embodiments, in both the delivery and deployed configurations can be generally smaller than that of existing devices, the strength of the tissue fixation device 100 remains sufficient to withstand the load to which it is subjected.

The substantially rigid first and second support members 102, 104 can vary in a number of ways. In the illustrated embodiment, as shown in FIG. 1C, the first and second support members 102, 104 are elongate discrete elements separated from each other and that are configured to provide structural support to the tissue fixation device 100 and thus to a graft. In the illustrated embodiment, the first and second support members 102, 104 are retained within retention passages or pockets 112, 114 formed from the flexible member 106. In other embodiments, the first and second support members 102, 104 can be coupled to the at least one flexible member 106 in other ways, as discussed below.

The support members 102, 104 can be generally cylindrical such that they can have a circular or oval cross-section. It should be appreciated that the embodiments described herein are not limited to a specific configuration of the support members 102, 104. For example, the support members 102, 104 can be generally planar such that they can have a rectangular or square cross-sectional shape. Furthermore, although each of the support members 102, 104 is shown in FIG. 1C as an elongate component having no features formed therethrough or thereon, in some embodiments, each support member can have various features. For example, in some embodiments, the first and second support members can include one or more surface features (e.g., ridges, prongs or other protrusions) that facilitate coupling of the support members to the flexible member. Furthermore, in embodiments wherein the flexible member is formed from multiple elongate filaments extending between the support members, the first and second support members can include retaining features to couple such elongate filaments thereto, as described in more detail below.

The first and second support members 102, 104 can remain substantially parallel to each other in both the delivery and deployed configurations. In the illustrated embodiment, the tissue fixation device 100 is configured such that the first and second support members 102, 104 may not translate or translate only slightly relative to one another. In other words, the first and second support members 102, 104 can remain at the same position with respect to one another along a length of the tissue fixation device 100.

The size of the first and second support members 102, 104 can vary in a number of ways. For example, the length of the first and second support members 102, 104, which determines the overall length of the tissue fixation device 100, can vary depending on the requirements of an intended application. Generally, the overall length is in the range of about 5 mm to about 25 mm. In yet other embodiments, the length can vary from about 10 mm to about 15 mm. In one embodiment, the length is about 12 mm. In the illustrated embodiments, the first and second support members 102, 104 have the same length. However, it is understood that the first and second support members 102, 104 can have different lengths. A diameter of a widthwise cross-section of the first and second support members 102, 104 can vary depending on the requirements of an intended application. In one aspect, the diameter can be in the range from about 0.5 mm to about 2.0 mm. In another aspect, the diameter can be in the range of about 1.0 to about 1.1 mm. When a widthwise cross-sectional shape of the support members 102, 104 is different from circular or oval, the size of the cross-section is similar to the above.

The first and second support members 102, 104 can be formed from any suitable material, and the individual members need not be formed from the same material. For example, they can be formed from a surgical stainless steel, titanium alloy, or another biocompatible, sufficiently strong metal that allows the first and second support members 102, 104 to withstand the load to which they will be subjected. In some embodiments, the first and second support members 102, 104 are formed from a Chromium Molybdenum (Co—Mo) alloy. The first and second support members 102, 104 can also be formed from non-metallic materials, which may be or may not be biodegradable materials. Non-limiting examples of such non-metallic materials include a polyether ether ketone (PEEK), polylactic acid (PLA), biphasic tricalcium phosphate (bTCP), and Biocryl® Rapide® material composed of 30% osteoconductive β-TCP and 70% polylactide co-glycolide (PLGA). In some embodiments, the first and second support members 102, 104 can be formed from ceramics, such as, for example, aluminum oxide. The first and second support members 102, 104 can be formed from one material or a combination of two or more materials. The materials typically have a high strength such that the Ultimate Tensile Strength is about 500 MPa and the Yield Strength is about 215 MPa. However, the materials can be such that their Ultimate Tensile Strength and the Yield Strength can have other values. The materials used to form the first and second support members 102, 104 can be such that the tissue fixation device 100 has a yield load in bending that varies from about 250 Newton (N) to about 2500 N, depending on a specific application. In one embodiment (e.g., in which the tissue fixation device 100 is used for an ACL replacement procedure), the yield load in bending of the tissue fixation device 100 can be about 1000 N.

The form and structure of the flexible member 106 connecting the first and second support members 102, 104 can vary in a number of ways. In the illustrated embodiment, as shown in FIG. 1A-1C, the flexible member 106 is in the form of a fabric sheet. However, in some embodiments, the flexible member 106 can be in the form of elongate connecting filaments extending between the rigid support members, as discussed in more detail below. Regardless of its specific configuration, the flexible member can be manipulated so as to change its configuration to thereby decrease a distance between the first and second support members 102, 104. In the illustrated embodiment, the flexible member 106 in the form of the fabric sheet can be rolled, bent, folded, collapsed, crimped, or otherwise manipulated so that a distance between the first and second support members 102, 104 can be decreased. In this way, a width of the tissue fixation device 100 can decrease. In such a configuration, the tissue fixation device 100 can be passed through a bone tunnel having a diameter that is less than a diameter that would be required to pass a conventional tissue fixation device therethrough.

The flexible member 106 can connect the first and second support members 102, 104 such that a distance at which the first and second support members 102, 104 are spaced apart is changeable in a number of ways. As shown in FIGS. 1A-1C, in the illustrated embodiment, the flexible member 106 has first and second retaining passages or pockets 112, 114 formed on either side of a longitudinal axis A of the tissue fixation device and which are configured to retain the first and second support members 102, 104 therein. It should be appreciated that FIG. 1A shows the first and second support members 102, 104 visible at the openings 112a, 112b of the first and second pockets 112, 114 for illustration purposes only. It is understood, however, that both openings of each of the pockets 112, 114 can be closed or closeable. In this way, the first and second support members 102, 104 are unable to slide out of the pockets 112, 114.

In the illustrated embodiment, the first and second pockets 112, 114 are formed by configuring the fabric forming the flexible member 106. For example, longitudinal sides of the fabric (which can be rectangular or square) can be rolled or folded towards a mid-portion of the fabric (which is also a mid-portion of the flexible member 106), and the folds can be stitched or otherwise secured to the remainder of the fabric to thereby form the longitudinal pockets. As shown in FIGS. 1A-1C, longitudinal stitches 116, 118 are formed at a distance spaced apart from opposite sides of the flexible member 106 to form the pockets 112, 114, respectively. In addition, transverse stitches 120a, 120b are formed to retain the first support member 102 within the first pocket 112, and transverse stitches 122a, 122b are formed to retain the second support member 104 within the second pocket 114. However, it should be appreciated that the first and second pockets 112, 114 can be formed in other ways, as embodiments described herein are not limited to a specific way of forming the pockets or otherwise retaining the support members. For example, the flexible member 106 can be manufactured such that it can have the pockets 112, 114 or other retaining features preformed and configured to receive and hold therein the first and second support members 102, 104.

Forming the pockets can involve placing the first and second support members 102, 104 at opposite longitudinal sides of the fabric and rolling or folding the sides of the fabric over the support members 102, 104, so as to enclose the support members 102, 104. Alternatively, the support members 102, 104 can be inserted into the pockets after the pockets are formed. Regardless of the specific way of forming the pockets, the first and second support members 102, 104 can each be held tightly within a respective pocket.

The flexible member can connect the first and second support members in other ways as well. For example, in some embodiments, the flexible member 106 can include a plurality of slits, holes or other openings along longitudinal sides thereof. To couple the first and second support members to one another, the flexible member can be passed through the openings, e.g., by entering the openings at alternating sides of the flexible member 106. Additionally or alternatively, as mentioned above, the first and second support members can include one or more surface features (e.g., ridges, prongs or other protrusions) that can facilitate interlocking between the support members and the flexible member. The first and second support members can be coupled to the flexible member in any other manner, such that the first and second support members do not separate from the flexible member during delivery and deployment of the device, and after the device is implanted.

The flexible member 106 can have various sizes and are dimensions (including length, width and thickness) and a person skilled in the art can readily determine the appropriate size depending on the requirements of a given application. The width (W) of the flexible member 106 in the original configuration of the tissue fixation device 100 (before delivery and deployment of the device 100) is shown in FIG. 1A and the width can range from about 2 mm to about 8 mm. In one embodiment, the width can be about 5 mm. The length (L) of the flexible member 106 shown in FIG. 1A can depend on the length of the first and second support members 102, 104. Thus, the flexible member 106 can be long enough to retain the first and second support members 102, 104 in the retaining pockets 112, 114. For example, the length (L) of the flexible member 106 can vary from about 5 mm to about 28 mm. In some aspects, the length can vary from about 10 mm to about 18 mm. In some aspects, the length can vary from about 12 mm to about 13 mm. In one aspect, the length (L) can be about 12 mm.

The flexible member 106 can be made from a number of suitable materials, such as biologically inert and biocompatible fabrics. For example, the flexible member 106 can be manufactured from fabrics such as polyethylene terephthalate (Dacron®) or polytetrafluoroethylene (PTFE, or GORE-TEX®). Alternatively, the flexible member 106 can be made from resorbable plastic fibers such as, for example, polylactic acid (PLA).

Referring back to FIGS. 1A-1C, as mentioned above, the tissue fixation device 100 includes the graft retention loop 108 coupled thereto. The graft retention loop 108 is configured (in size, shape and strength) to hold a tissue graft passed through the loop when the tissue fixation device 100 is implanted. In the illustrated embodiment, the graft retention loop 108 is coupled to the flexible member 106 and disposed around the rigid support members 102, 104. The graft retention loop 108 can be coupled to the flexible member 106 by passing therethrough. As shown in FIG. 1C, the graft retention loop 108 can be formed from a suture or a similar material having its opposite free ends coupled together at a knot 109. It should be appreciated that, the knot 109 can be formed after the suture is passed through the flexible member 106. It should also be appreciated that the graft retention loop 108 can be coupled to the flexible member 106 using techniques that may not involve forming a knot. For example, the loop can be a continuous loop, or the ends of the suture forming the loop can be joined together using a lap joint, splice joint, or other technique. Additionally or alternatively, the ends of the suture can be glued together. Any other technique can be used as embodiments are not limited in this respect.

The graft retention loop 108 can have any suitable dimensions. For example, in some embodiments, it can have a length (before forming a loop) in the range of about 10 mm to about 60 mm. In some embodiment, the length can range from about 15 mm to about 20 mm. In one embodiment, the length can be about 25 mm. The length of the graft retention loop 108 can be fixed. Alternatively, in some embodiments, the length of the graft retention loop 108 can be adjustable such that it can be changed by a user when the tissue fixation device 100 is in use. For example, the graft retention loop 108 can be manipulated to increase its length when a longer loop is desired. As another example, a length of the graft retention loop 108 can be decreased if the original length is longer than desired.

The thickness (diameter) of the material forming the loop can also vary and it is typically in the range from about 1 mm to about 4 mm. Also, the graft retention loop 108 can be formed from any suitable material(s) and it can be formed in a number of ways. For example, it can be a continuous loop or it can be braided, woven, or otherwise formed construct. A person skilled in the art will appreciate that any variety of materials (including ultra-high-molecular-weight polyethylene (UHMWPE)) can be used to form the loop, including those typically used to form sutures. Further, the tensile strength at break can be about 50 MPa and the tensile strength at yield can be about 20 MPa such that the material is sufficiently strong to serve its intended purpose of graft retention. The maximum tensile load of the entire construct can be in the range from about 250 N to about 2500 N. It should be appreciated that the described embodiments are not limited to any specific graft retention loop.

The graft retention loop 108 can be formed from any suitable materials. For example, the loop 108 can be formed from a suture that can be any type of suture. For example, the suture can be from size 0 to size 5, such as Orthocord® suture or Ethibond® suture. In some embodiments, the suture can be formed from ultra-high-molecular-weight polyethylene (UHMWPE). In some embodiments, the suture can include high-molecular weight-polyethylene (HMWPE) or HMWPE with a co-braid (e.g., monofilament polypropylene, nylon or other co-braid). In some embodiments, monofilament sutures such as, for example, Monocryl® available from Ethicon, Inc., may be utilized. As another example, an absorbable suture such as Vicryl® (a copolymer made from 90% glycolide and 10% L-lactide) also available from Ethicon, Inc. may be used. The sutures used herein can have any suitable amount and type of bioabsorbable material, which can depend on a particular surgical procedure and/or surgeon preferences.

As shown in FIGS. 1A-1C, the flexible member 106 includes apertures or openings 124, 126, formed at opposite sides of the longitudinal axis A of the flexible member 106, and these are intended for passing the graft retention loop 108 therethrough so as to couple the loop 108 to the tissue fixation device 100. The openings 124, 126 can be pre-formed or they can be formed as a suture forming the graft retention loop 108 is passed through the flexible member 106. The openings 124, 126 can be reinforced by additional sutures placed around their perimeter, or in any other manner, so as to prevent fabric forming the flexible member 106 from fraying and improve the rigidity of the openings.

It should be appreciated that the two openings 124, 126 formed through the flexible member 106 are shown by way of example only, as a single openings can be formed. As another example, the loop 108 can wrap around the tissue fixation device 100, without passing through the flexible member. In some embodiments, a tissue fixation device can include a graft retention loop can be formed from a flexible member. For example, the flexible member can be tied to form a loop and it can be otherwise configured into a loop-like shape.

The tissue fixation device 100 also includes leading and trailing sutures 110, 111 that assist in passing the device 100 through the bone tunnel and in "flipping" device 100 after it is passed through the tunnel, as discussed in more detail below. The leading and trailing sutures 110, 111 can have any suitable length and can be formed from any suitable materials. For example, in some embodiments, the leading suture 110 can be formed from ultra-high-molecular-weight polyethylene (UHWMPE) high strength Orthocord® suture size 5, and the trailing suture 111 can be formed from ultra-high-molecular-weight polyethylene (UHWMPE) high strength Orthocord® suture size 2. In some embodiments, one or both of the leading and trailing sutures can be from size 0 to size 5, such as Orthocord® suture commercially available from DePuy Mitek, and Ethibond® suture available from Ethicon, Inc. However, a person skilled in the art will appreciate that the leading and trailing sutures 110, 111 can be formed from any suitable materials, including from the same type of suture.

The leading and trailing sutures 110, 111 can be coupled to the tissue fixation device 100 in a number of ways. In the illustrated embodiment, as shown in FIGS. 1A-1C, the flexible member 106 includes apertures or openings 130, 131 for passing the leading and trailing sutures 110, 111 therethrough. As shown, the openings 130, 131 are formed at opposite sides thereof and disposed approximately along the longitudinal axis A of the flexible member 106. Like openings 124, 126 for retaining the loop 108, the openings 130, 131 can be pre-formed in the flexible member 106 or they can be formed as the leading and trailing sutures 110, 111 are passed through the flexible member 106 (e.g., using a needle). The openings 130, 131 can be reinforced in a suitable manner.

Figure 2A:
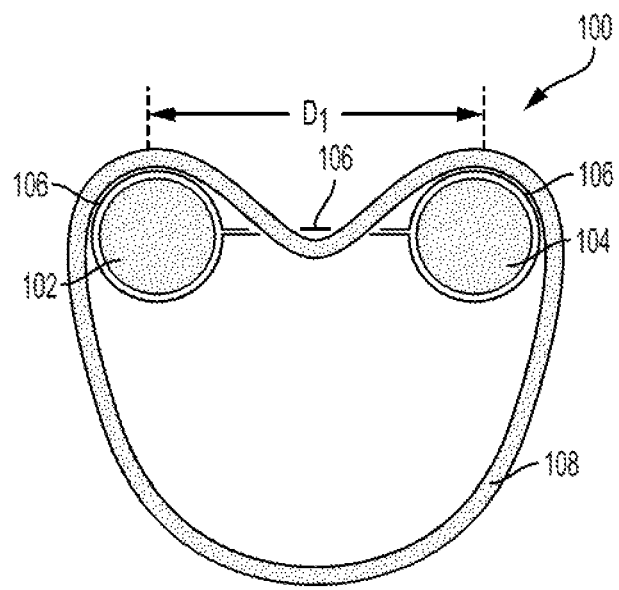
FIG. 2A is a side cross-sectional view of the tissue fixation device of FIG. 1A in an uncompressed configuration.
Figure 2B:
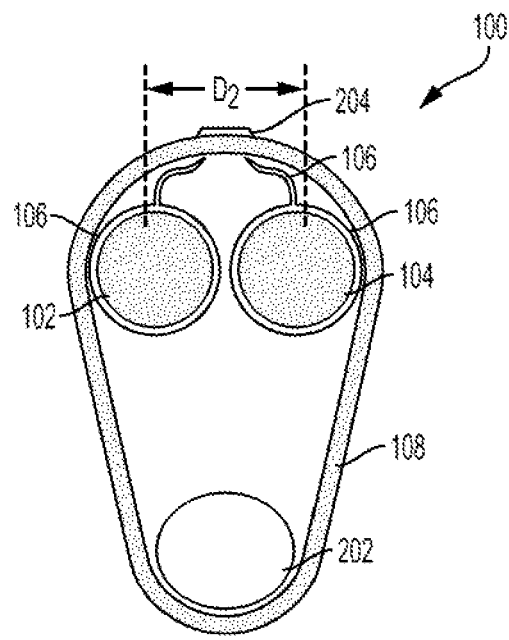
FIG. 2B is a side cross-sectional view of the tissue fixation device of FIG. 2A in a compressed configuration.

As indicated above, the tissue fixation device 100 is configured such that the flexible member 106 can be folded, crimped, or otherwise deformed and the distance between the rigid support members 102, 104 can thus decrease relative to the original (undeformed or uncompressed) configuration of the device to facilitate delivery. FIGS. 2A and 2B illustrate the tissue fixation device 100 in an original, uncompressed configuration (FIG. 2A) and in a compressed configuration (FIG. 2B), which can be a deployed and/or delivery configuration. As shown, in the original configuration, the rigid support members 102, 104 can be disposed such that a distance D1 between their mid-points is greater than a distance D2 between the mid-points in the compressed configuration. The tissue fixation device 100 can be passed through a bone tunnel in the compressed delivery configuration in which the rigid support members 102, 104 maintained in a non-intersecting orientation with respect to one another, as shown in FIG. 2B. In the delivery configuration, the rigid support members 102, 104 are disposed close to each other such that the tissue fixation device 100 can be passed through a bone tunnel having a reduced diameter.

After the tissue fixation device 100 is passed through the bone tunnel, as discussed in more detail below, it is placed over an opening in a bone tunnel (not shown) in the compressed deployed configuration such that the graft retention loop 108 is used to retain a tissue graft 202. Thereafter, the device can be rearranged in a manner desired by the surgeon. Typically, because the tissue graft 202 is tensioned due to load applied thereto such that the graft loop 108 extends into the bone tunnel, the rigid support members 102, 104 tend to be brought closer together as the flexible member 106 forms one or more folds 204. As the rigid support members 102, 104 come closer together, they are maintained in a non-intersecting orientation with respect to one another. It should be appreciated that, in the delivery configuration, the rigid support members 102, 104 can be positioned closer to one another as compared to their relative positions in the original, uncompressed configuration. Thus, a distance between the mid-points of the rigid support members 102, 104 in the delivery configuration can be equal or greater than D2 and less than D1. However, in some embodiments, in the delivery configuration, the rigid support members 102, 104 can be positioned with respect to one another such that a distance between their mid-points is approximately equal to the distance D1 in the uncompressed configuration of the tissue fixation device 100.

Figure 3A:
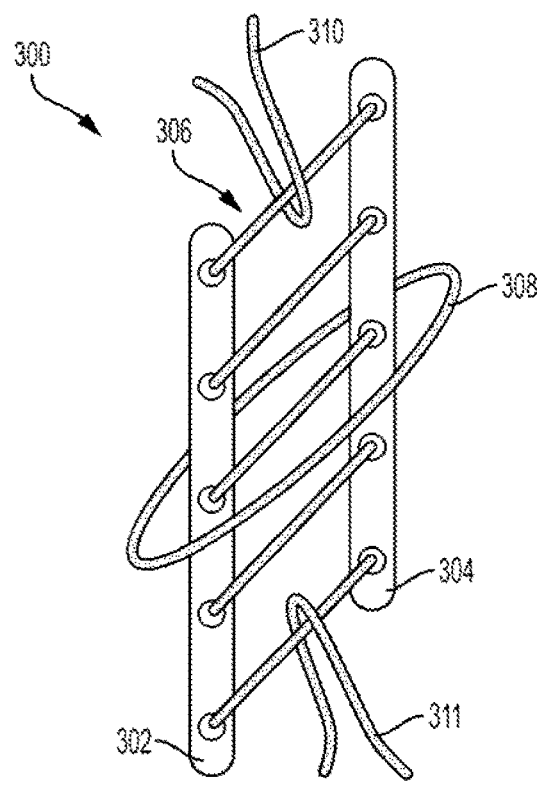
FIG. 3A is a plan view of another embodiment of a tissue fixation device in an undeployed configuration prior to the device being passed through a femoral tunnel.
Figure 3B:
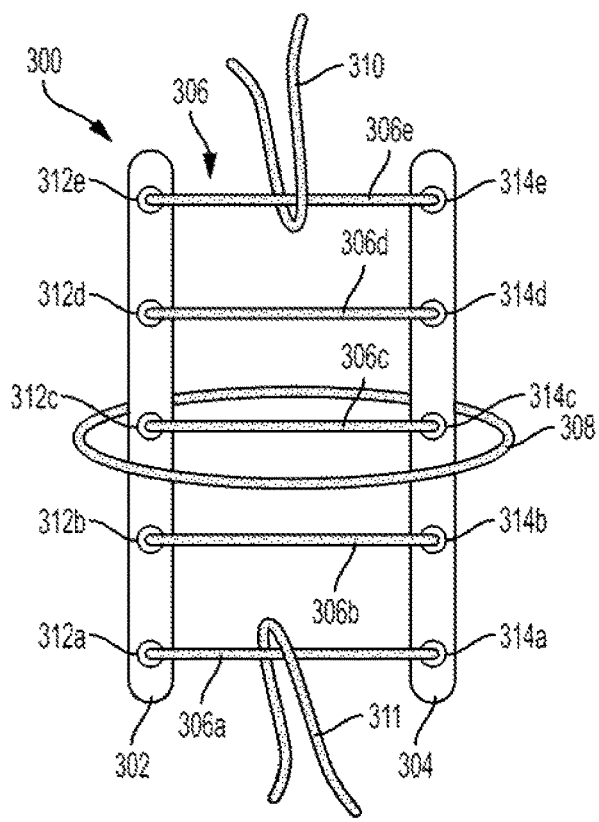
FIG. 3B is a perspective view of the tissue fixation device of FIG. 3A in an undeployed configuration in which the device is passed through a femoral tunnel.

FIGS. 3A and 3B illustrate another embodiment of a tissue fixation device 300 including first and second substantially rigid support members 302, 304 and a flexible member 306 in the form of a plurality of elongate connecting filaments 306a-306e extending between the rigid support members 302, 304. Like tissue fixation device 100 (FIGS. 1A-1C), the tissue fixation device 300 also includes a graft retention loop 308 coupled thereto such that it passes around both sides of the device, and leading and trailing sutures 310, 311 also coupled thereto.

The first and second rigid support members 302, 304 are substantially elongate elements coupled to one another via the flexible member 306 such that a distance between the support members 302, 304 is changeable. Each of the rigid support members 302, 304 can include a plurality of retaining elements used to couple the elongate connecting filaments 306a-306e thereto. Thus, as shown in FIGS. 3A and 3B, the first support member 302 includes first retaining elements 312a-312e, and the second support member 304 includes second retaining elements 314a-314e. In the illustrated embodiment, the first and second retaining elements 312a-312e, 314a-314e are in the form of openings formed in the rigid support members 302, 304 and longitudinally spaced along a length of the support members 302, 304. The first retaining elements 312a-312e can be spaced the same distance apart along the first support member 302, and the second retaining elements 314a-342e can be similarly spaced the same distance apart along the second support member 304.

The openings can have a round or oval cross-sectional shape, and they can be formed such that, in the original configuration, an opening in one of the support members is disposed opposite to an opening in another one of the support members. A person skilled in the art will appreciate, however, that the openings 312a-312e, 314a-314e can be formed in the rigid support members 302, 304 in other manners, as embodiments are not limited in this respect. Furthermore, retaining elements having other configurations (e.g., hooks, protrusions or other structures) can be formed on or within the support members 302, 304.

The first and second rigid support members 302, 304 can be sized and constructed similar to first and second rigid support members 102, 104 (FIGS. 1A-1C), as discussed above. Also, the first and second rigid support members 302, 304 can be formed from materials similar to those used to form the first and second rigid support members 102, 104 which are also discussed above.

In the illustrated embodiment, the elongate connecting filaments 306a-306e connecting the first and second rigid support members 302, 304 can each be formed from a separate element (e.g., suture or wire) such that the tissue fixation device 300 has an overall "ladder-like" configuration. However, in some embodiments, a single suture or wire element can be passed through the openings 312a-312e, 314a-314e or coupled to via other retaining elements to the rigid support members 302, 304. The single suture can be used to form a tissue fixation device having "ladder-like" configuration or a tissue fixation device in which elongate connecting filaments from a crisscrossed pattern between the support members.

The connecting filaments 306a-306e can be rigid such that, in a delivery configuration, the distance between the rigid support members 302, 304 can decrease as they translate with respect to each other, as shown in FIG. 3B. In embodiments in which the connecting filaments 306a-306e are formed from a flexible suture, wire, or other material(s), the connecting filaments 306a-306e can be deformed in a manner similar to flexible member 206 (FIGS. 2A and 2B) to allow the rigid support members 302, 304 to come closer together without translating with respect to each other.

As mentioned above, the connecting filaments 306a-306e of the flexible member 306 can be formed from a suture or wire. The suture can be any type of suture. For example, the suture can be from size 0 to size 5, such as Orthocord® suture or Ethibond® suture. In some embodiments, the suture can be formed from ultra-high-molecular-weight polyethylene (UHMWPE). In some embodiments, the suture can include high-molecular weight-polyethylene (HMWPE) or HMWPE with a co-braid (e.g., monofilament polypropylene, nylon or other co-braid). In some embodiments, monofilament sutures such as, for example, Monocryl® available from Ethicon, Inc., may be utilized. As another example, an absorbable suture such as Vicryl® (a copolymer made from 90% glycolide and 10% L-lactide) also available from Ethicon, Inc. may be used. The sutures used herein can have any suitable amount and type of bioabsorbable material, which can depend on a particular surgical procedure and/or surgeon preferences. In embodiments in which the connecting filaments 306a-306e are formed from a wire, the wire can be formed from surgical stainless steel, titanium alloy, or other biocompatible metal, or polymer.

As shown in FIGS. 3A and 3B, the graft retention loop 308 can be coupled to the tissue fixation device 300 by being disposed around the rigid support members 302, 304. The graft retention loop 308 can additionally or alternatively be coupled to the rigid support members 302, 304 in a number of other ways. For example, the graft retention loop 308 can be coupled to a feature (not shown) formed on or in one or both of the support members 302, 304. As another example, the graft retention loop 308 can be coupled to the rigid support members 302, 304 by passing around or through one of the flexible filaments 306a-306e, for example, around or through the filament 306c or one or more of other filaments.

The leading and trailing sutures 310, 311 can be coupled to the tissue fixation device 300 in a number of ways. For example, the leading and trailing sutures 310, 311 can pass around one or more of the elongate connecting filaments 306a-306e. Thus, in the illustrated embodiment, as shown in FIGS. 3A and 3B, the leading and trailing sutures 310, 311 are coupled to the tissue fixation device 300 such that the leading suture 310 passes (e.g., loops) around the connecting filament 306e at one end of the device 300 and the trailing suture 311 passes (e.g., loops) around the connecting filament 306a at the opposite end of the device 300. It should be appreciated that the locations of the leading and trailing sutures can be reversed such that the leading suture 310 passes around the connecting filament 306a and the trailing suture 311 passes around the connecting filament 306e. Furthermore, as a person skilled in the art will appreciate, the leading and trailing sutures 310, 311 can be coupled to the tissue fixation device 300 in other ways. For example, one or both of the leading and trailing sutures 310, 311 can pass through one or more of the elongate connecting filaments 306a-306e. Also, the leading and trailing sutures can loop more than one time about one or more of the elongate connecting filaments 306a-306e.

The leading and trailing sutures 310, 311 can be formed from materials similar to those used to form leading and trailing sutures 110, 111 of tissue fixation device 100 (FIGS. 1A-1C), as discussed above.

Figure 4:
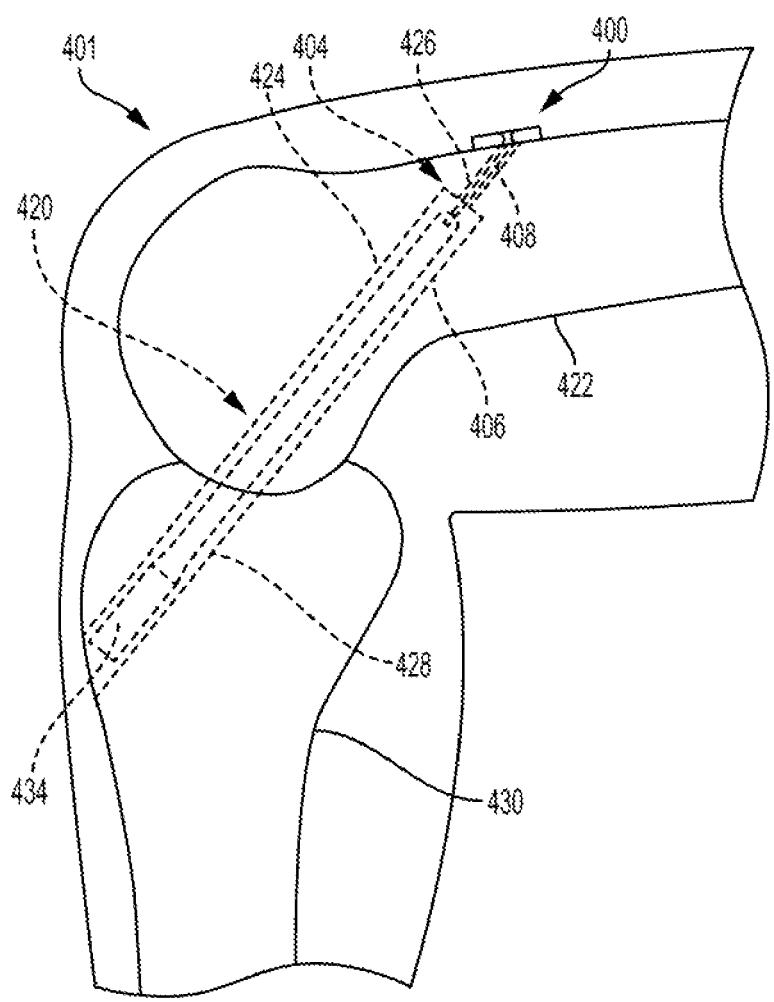
FIG. 4 is a side elevation cross-sectional view of a knee having an ACL reconstruction procedure using a tissue fixation device in accordance with some embodiments.

Some embodiments provide a method for fixating a graft tendon into a bone tunnel using the tissue fixation device described herein. FIGS. 4, 5A-5D and 6 illustrate one embodiment of such method used, for way of example, in an ACL reconstruction procedure. FIG. 4 illustrates a patient's leg 401 having an ACL reconstruction procedure performed thereon using a tissue fixation device 400, such as tissue fixation device 100 (FIGS. 1A, 1B, 2A, and 2B) or tissue fixation device 300 (FIGS. 3A and 3B). The tissue fixation device 400 can include first and second substantially rigid support members 402, 404, at least one flexible member 406 coupled therebetween, a graft retention loop 408, and leading and trailing sutures 410, 411.

The method involves forming a graft construct 404 by coupling a graft tendon 406 to a tissue fixation device via the graft retention loop 408 of the tissue fixation device 400. The graft tendon 406 can pass over the graft retention loop 408. It should be appreciated that in FIGS. 5A-5D the graft tendon 406 is shown not to scale, because the graft tendon 406 is actually thicker such that it substantially entirely fills the bone tunnel (e.g., a femoral socket 424) receiving it. The graft tendon 406, once implanted, contacts the bone in which the bone tunnel is formed such that the graft 406 grows into and merges with the bone for a permanent repair.

FIG. 4 shows the graft construct 406 in place in the patient's leg 401. The graft tendon 406 can be any suitable type of graft. For example, an autograft, which is a portion of the patient's own tissue that would replace the damaged natural ligament, can be used. The autograft is often a hamstring tendon, though other tendons can be used (e.g., a patellar tendon). The tendon graft can also be an allograft obtained from a donor. The graft tendon 406 can be prepared in a suitable manner well known to those skilled in the art, which can involve cleaning and measuring the graft, and then reinforcing free ends thereof.

Surgical techniques for ligament reconstruction are well known. Generally, the method includes forming a bone tunnel to receive the graft tendon 406 therein. A bone tunnel for an ACL reconstruction procedure in a patient's leg can be formed by drilling a tibial tunnel through the tibia, as known in the art. A femoral tunnel is then drilled such that diameters of the femoral and tibial tunnels are appropriate to snugly fit the graft construct therethrough. In the embodiments described herein, because of the smaller size of the tissue fixation device 400 as compared to existing devices, a passing tunnel having a diameter that is less than a diameter of a passing tunnel required to pass therethrough a conventional device can be formed.

In the illustrated embodiment, as shown in FIGS. 4 and 5A-5D, a bone tunnel 420 in the patient's leg 401 is formed that includes a femoral tunnel or socket 424 and a tibial tunnel 428. In the illustrated embodiment, a drill pin, such as a Beath pin or other instrument, is used to drill a relatively narrow bone tunnel through the femur 422. A diameter of such bone tunnel drilled using the pin can be in the range of about 1 mm to 4 mm. In one embodiment, the tunnel diameter is about 2.4 mm. This step forms a passing tunnel 426 shown in FIGS. 4 and 5A-5D that extends from the condylar notch of the femur laterally to the lateral cortex. Next, the larger diameter tunnel 424 can be formed through the femur 422 sized so as to receive the graft ligament 406 therethrough. This femoral tunnel can be formed using, for example, a cannulated drill advanced over the Beath pin, or using any other technique as known in the art. FIG. 4 illustrates a tunnel 420 in the leg's femur 422 including such larger diameter inferior portion or femoral socket 424 sized to accommodate the graft ligament 406 and a smaller diameter superior portion or passing channel or tunnel 426 sized to accept the tissue fixation device 400 in a delivery configuration. The diameter of the femoral socket 424 can be in the range of about 6 to about 12 mm. In one embodiment, the diameter of the femoral socket is about 9 mm.

In the illustrated embodiment, after the femoral socket 424 is formed, the formation of the bone tunnel for the procedure is complete. As indicated above, the passing tunnel 426 is formed in the femur superiorly to the femoral socket 424 by drilling the Beath pin or other similar instrument through the femur. Thus, it is not required to form a separate passing tunnel. In contrast, a technique using a conventional tissue fixation device would require an additional step of forming a larger passing tunnel having a diameter, e.g., about 4.5 mm.

Figure 5A:
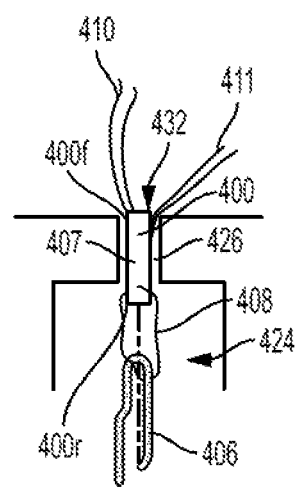
FIGS. 5A-5D are sequential side elevation cross-sectional views of a bone tunnel during an ACL reconstruction procedure using the tissue fixation device of FIG. 4.

FIG. 5A illustrates that the tissue fixation device 400 can be passed through the femoral socket 424 and passing tunnel 426 such that the graft retention loop 408 extends downward into the bone tunnel. With the graft retention loop 408 extending into the bone tunnel, the tissue fixation device 400 is passed through the passing tunnel 426 in a delivery configuration. In such a configuration, the substantially rigid support members 402, 404 (shown in FIG. 6) are disposed in a non-intersecting orientation relative to one another. Thus, the rigid support members 402, 404 can be substantially parallel to one another as they are passed through the femoral socket 424 and then through the passing tunnel 426. In the delivery configuration, the rigid support members 402, 404 are disposed a first distance away from one another that is less than a distance between the rigid support members 402, 404 in an original configuration. This reduced distance between substantially rigid support members 402, 404 allows the support members 402, 404 and flexible member 406 coupled therebetween to pass through the passing tunnel 426 having a reduced diameter. For example, the passing tunnel 426 can have a diameter of in the range of about 2.4 mm to about 2.9 mm, which corresponds to an outer diameter of a drill pin (e.g., a Beath pin) used to form the passing tunnel 426.

As shown in FIG. 5A, the tissue fixation device can be advanced through the bone tunnel with a first end 400f of the first and second ends 400f, 400r thereof being a forward end.

Figure 5B:
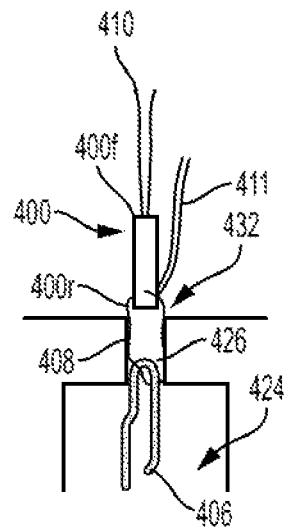
Figure 5C:
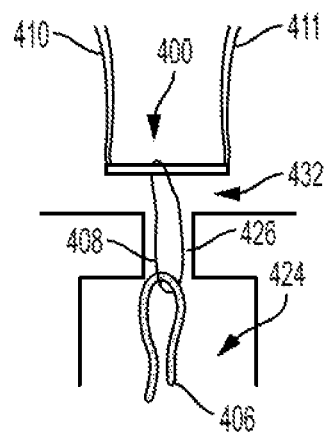

The first, forward end 400f has the leading suture 410 extending therefrom, while the second end 400r has the trailing suture 411 extending therefrom, as shown in FIGS. 5A-5C. For example, tension can be applied to the leading suture 410 to cause the first end 400f to move upwardly out of the passing tunnel 426 until the first end 400f emerges from the passing tunnel 426.

The tissue fixation device 400 is passed through the passing tunnel 426 until the rigid support members 402, 404 and flexible member 406 extend beyond the lateral cortex of the femur 422, above an opening 432 of the passing tunnel 426, as shown in FIG. 5B. As shown in FIG. 5C, the tissue fixation device 400 is then "flipped" such that the rigid support members 402, 404 are positioned over and across the opening 432. For example, tension can be applied to the second suture 411 such that the tissue fixation device 400 moves into a configuration as shown in FIG. 5C.

Figure 5D:
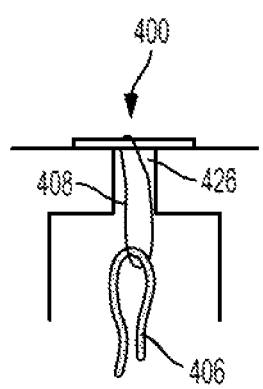

Next, after the graft construct 404 is disposed over the opening 432 in the bone tunnel, the tissue fixation device 400 can be positioned over the opening 432 in a deployed configuration as shown in FIG. 5D. As shown in FIG. 5D, in the deployed configuration, the graft retention loop 408 and the graft ligament 406 coupled thereto extend into the bone tunnel. In the deployed configuration, the rigid support members 402, 404 are disposed a second distance away from one another that can be greater than the first distance between the rigid support members 402, 404 in the delivery configuration. In the deployed configuration, as shown in FIG. 6, the rigid support members 402, 404 remain disposed in the non-intersecting orientation relative to one another.

While the distance between the rigid support members 402, 404 in the deployed configuration is greater than that in the delivery configuration, the distance between the rigid support members 402, 404 in the deployed configuration can be less than a distance between the rigid support members 402, 404 in the original configuration of the tissue fixation device 400. Tension applied to the graft ligament 406 during the procedure causes tension to be also applied to tissue fixation device 400 such that the rigid support members 402, 404 come closer together. The flexible member 406 can be in a configuration (e.g., deformed, folded, crimped, etc.) that is different from its original configuration so as to allow the distance between the rigid support members 402, 404 to decrease relative to that in the original. However, in some embodiments, the distance between the rigid support members 402, 404 in the deployed configuration can be the same as that in the original configuration of the tissue fixation device 400.

The support members 402, 404 can be positioned over the opening 432 in any orientation, however they generally do not intersect. Although the support members 402, 404 are substantially rigid, they can have some degree of flexibility or malleability such that the tissue fixation device 400 can be positioned over the opening 432 so as to conform to the shape of the lateral cortex. In this way, as mentioned above, the tissue fixation device 400, once implanted, can be less palpable as compared to existing devices. In the deployed configuration, as shown in FIGS. 4, 5D, and 6, the tissue fixation device 400 sits against the femur 422 in a sideways orientation with the graft retention loop 408 and the graft 406 extending medially through the passing tunnel 426 and into the socket 424. The graft retention loop 408 passes around both sides of the tissue fixation device 400 such that it is supported by both the support members 402, 404. However, in some cases, the graft retention loop can pass over one side of the device so as to be supported by one of the support members. An opposite end of the graft 406 can be placed into a tibial tunnel 428 in the leg's tibia 430 and held in place with a suitable anchor 434, as is known in the art. After the tissue fixation device 400 is implanted, the leading and trailing sutures can be removed, as shown in FIG. 5D.

Figure 6:
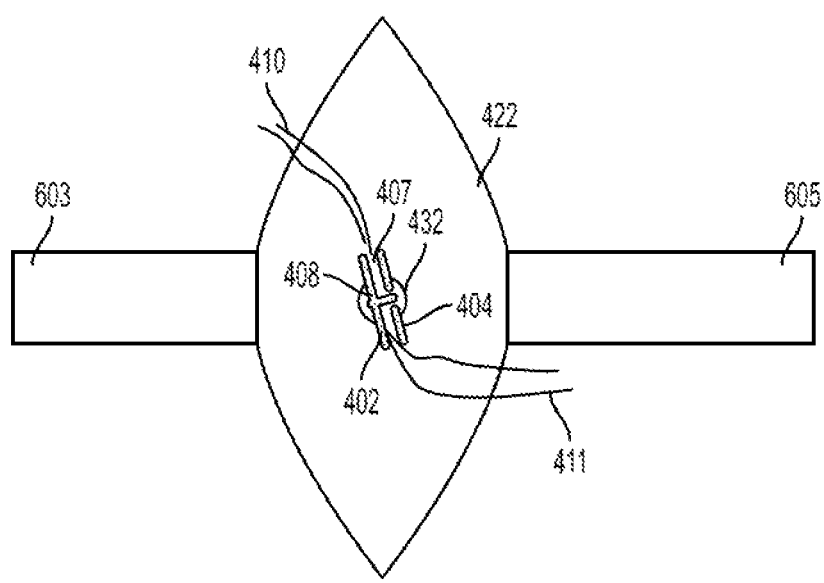
FIG. 6 is a schematic top view of the tissue fixation device of FIG. 4 deployed on the lateral cortex of the femur to retain a graft in the bone tunnel as shown in FIGS. 5A-5D.

FIG. 6 shows the tissue fixation device in the deployed configuration in which the tissue fixation device 400 extends over the opening 432 in the passing tunnel in the femur 422. As mentioned above, the rigid support members 402, 404 are disposed in a non-intersecting orientation with respect to one another. FIG. 6 shows by way of example only retracting instruments 603, 605 that would be used to retract tissue to view the implanted tissue fixation device 400.

Figure 7:
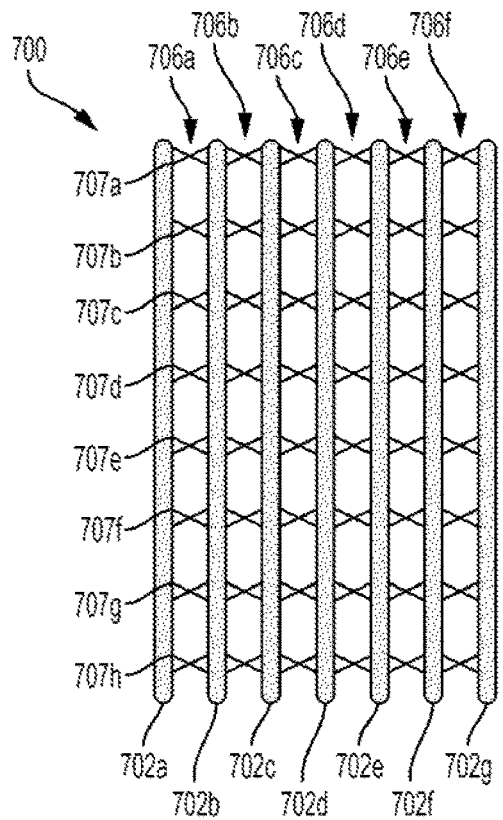
FIG. 7 is a perspective view of an embodiment of a tissue fixation device including multiple rigid support members.

In some embodiments, a tissue fixation device has more than two rigid support members. In such embodiments, the rigid support members can have a reduced diameter such that the tissue fixation device can move to a compressed configuration by being rolled into a tube-like configuration. FIG. 7 illustrates an implantable tissue fixation device 700 that includes a plurality of substantially rigid elongate support members 702a-702g and a plurality of flexible members 706a-706f each connecting two of the support members 702a-702g. Although not shown, the tissue fixation device 700 also has at least one graft retention loop (which can be similar to graft retention loop 108 of FIGS. 1A-1C) coupled to one or more of the flexible members 706a-706g in a suitable manner. The tissue fixation device 700 can also have one or both of leading and trailing sutures coupled to opposite ends thereof.

As mentioned above, the rigid support members 702a-702g can have a small diameter, for example, about 0.1 mm. It should be appreciated that seven rigid support members 702a-702g are shown in FIG. 7 by way of example only, since the tissue fixation device 700 can have other number of rigid support members (e.g., three, four, five, six, eight or more than eight). The larger the number of the rigid support members, the smaller the diameter of each of the rigid support members. The rigid support members 702a-702g are connected to each other via flexible members 706a-706g such that the rigid support members 702a-702g remain in a non-intersecting orientation with respect to one another in uncompressed and compressed configurations.

As shown in FIG. 7, each of the flexible members 706a-706g connecting respective two of the rigid support members 702a-702g includes multiple filaments. For example, the flexible member 706a can be in the form of a plurality of filaments 707a-707h as shown in FIG. 7. In the illustrated embodiment, the filaments 707a-707h can be spaced at approximately equal distances away from each other along a length of the rigid support members 702a-702g. However, the filaments 707a-707h can be disposed along a length of the rigid support members 702a-702g at other intervals.

As shown, each of the filaments 707a-707h can include one or more elements movably coupled to each other. In the illustrated embodiment, each of the filaments is in the form of two triangular-shaped elements connected to one another so as to form a cross-hatching pattern. The filaments can also be formed by interconnected rings or any other elements. It should be appreciated that eight filaments 707a-707h together forming a flexible member are shown in FIG. 7 by way of example only, as the rigid support members 702a-702g can be coupled to one another using any suitable number of any other type(s) of filaments. The filaments can be formed from a metal, fabric or any other material.

The support members 702a-702g are connected via the flexible members 706a-706g such that adjacent support members can be displaced with respect to each other. The support members 702a-702g can be connected via the flexible members 706a-706g such that the support members 702a-702g at least partially restricted from translating with respect to one another. Alternatively, the flexible members 706a-706g can connect the support members 702a-702g such that adjacent support members 702a-702g can be translated with respect to one another.

The tissue fixation device 700 can move from an uncompressed to a compressed configuration by being rolled into a tube-like configuration. In such configuration, the tissue fixation device 700 can be passed through a bone tunnel (e.g., a femoral tunnel) having a relatively small diameter. For example, the tissue fixation device 700 can be passed in the compressed configuration through femoral socket 424 and passing tunnel 426 shown in FIGS. 4, and 5A-5D. After the tissue fixation device 700 passes through the bone tunnel, the device 700 can be moved to an uncompressed or partially uncompressed configuration to support the tissue fixation loop and a graft coupled thereto. For example, the tissue fixation device 700 can be unrolled into a flat or partially flat configuration.

Figure 8:
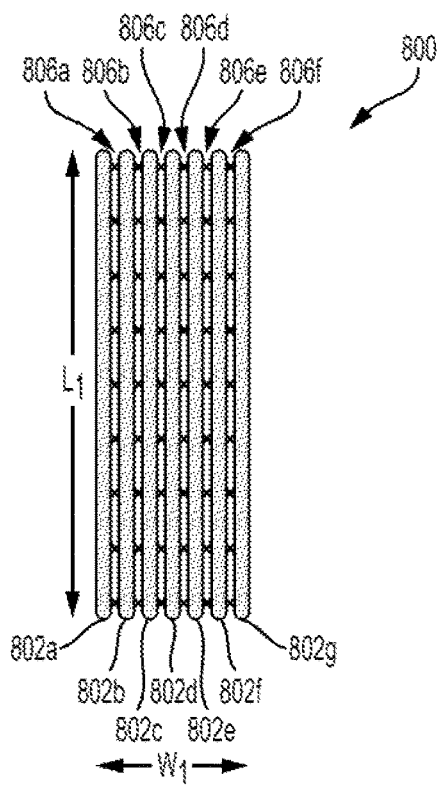
FIG. 8 is a perspective view of another embodiment of a tissue fixation device including multiple rigid support members.

FIG. 8 illustrates another embodiment of a tissue fixation device 800 which is similar to tissue fixation device 700 (FIG. 7). As shown, the tissue fixation device 800 includes a plurality of substantially rigid elongate support members collectively referred to as rigid elongate support members 802 and a plurality of flexible members each connecting two of the support members 802 and collectively referred to as flexible members 806. The flexible members 806 can be similar to the flexible members 706a-706g (FIG. 7) or they can have other configuration.

In the illustrated embodiment, as shown in FIG. 8, a distance between each adjacent support members 802 can be relatively small. The width (W1 in FIG. 8) of the tissue fixation device 800 in the original configuration (before delivery and deployment of the device 800) can range from about 2 mm to about 8 mm. In one embodiment, the width can be about 5 mm. The length (L1 in FIG. 8) of the tissue fixation device 800 can depend on the length of the rigid elongate support members 802 and it can vary from about 5 mm to about 28 mm. In some embodiments, the length L1 can vary from about 10 mm to about 18 mm. In some embodiments, the length can vary from about 12 mm to about 13 mm. In one embodiment, the length L1 can be about 12 mm. A width of each of the flexible members 806 can depend on a diameter of the support members 702a-702g. For example, in embodiments in which the diameter of each of the support members 702a-702g is about 0.1 mm, the width of each of the flexible members 806 can vary from about 0.03 mm to about 0.08 mm.

Figure 9A:
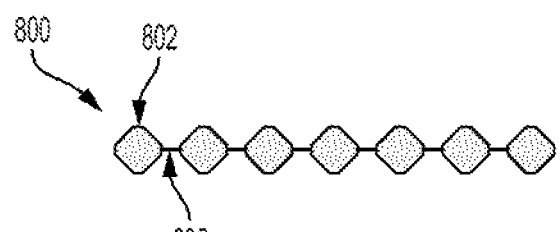
FIG. 9A is a schematic side view of the tissue fixation device of FIG. 8 in an uncompressed configuration.
Figure 9B:
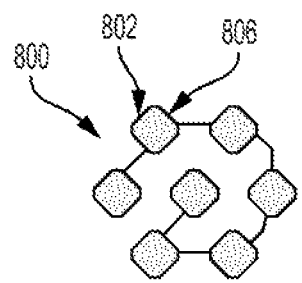
FIG. 9B is a schematic side view of the tissue fixation device of FIG. 8 in a compressed configuration.

The tissue fixation device 800 can be used in the same manner as tissue fixation device 400 (FIGS. 4 and 5A-5D) and the use of the device 800 is therefor is not discussed in detail herein. FIG. 9A shows the tissue fixation device 800 in an uncompressed configuration, and FIG. 9B shows an exemplary embodiment of the tissue fixation device 800 in a compressed (rolled-up) configuration. The tissue fixation device 800 can be delivered to an implantation site in such a configuration.

Figure 9C:
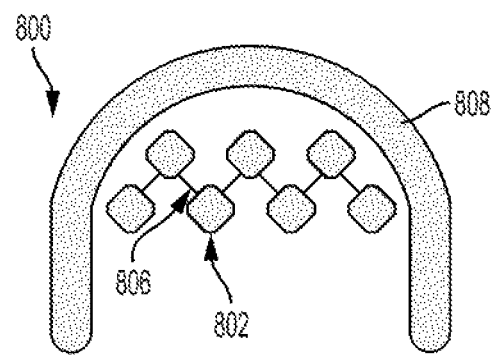
FIG. 9C is a schematic side view of the tissue fixation device of FIG. 8 having a load applied thereto.

FIG. 9C illustrates the tissue fixation device 800 in the deployment configuration, with a graft retention loop 808 coupled thereto in a suitable manner. As shown in FIG. 9C, because a tissue graft (not shown) coupled to the graft retention loop 808 is tensioned due to load applied thereto, the rigid support members 802 tend to be brought closer together as the flexible members 806 allow the rigid support members 802 to be replaced with respect to one another. Thus, in such configuration, the tissue fixation device 800 is no longer in the rolled-up into a tube and, at the same time, the device 800 has a configuration different from a fully flattened configuration, as shown in FIG. 9B. A person skilled in the art will appreciate that the tissue fixation device 800 is shown in FIGS. 9B and 9C by way of example only and that the tissue fixation device 800 can be compressed in different other ways in its deployment and delivery configurations.

It should be appreciated that although illustrated embodiments provide devices and methods for orthopedic surgeries, such as, for example, ligament reconstruction surgery involving fixation of anterior or posterior cruciate ligaments, the techniques can be adapted for other surgical procedures as well. For example, the described devices and methods can be used for acromioclavicular joint reconstruction and ankle syndesmosis. The devices and methods can be used for anastomosis and other surgeries where it is required to bring together two (or more) soft tissues, soft tissue and bone tissue, or two bone tissues need to be brought or held together.

Having thus described some examples of the described embodiments, various alterations, modifications, and improvements will readily occur to those skilled in the art. Such alterations, modifications, and improvements are intended to be within the spirit and scope of the described embodiments. Accordingly, the foregoing description is by way of example only, and not intended to be limiting.

What is claimed is:

1. An implantable tissue fixation device, comprising:
   first and second elongate support members that are distinct elements;
   at least one flexible connecting member connecting the first and second elongate support members, the tissue fixation device having changeable dimensions such that the device has a delivery configuration and a deployed configuration, wherein the tissue fixation device has at least one dimension that is smaller in the delivery configuration than in the deployed configuration, wherein the first and second elongate support members are parallel and spaced apart from each other in the deployed configuration; and
   at least one graft retention loop coupled to the tissue fixation device.

2. The implantable tissue fixation device of claim 1 wherein the graft retention loop is operably connected to at least one elongate support member.

3. The implantable tissue fixation device of claim 1, wherein the graft retention loop encircles the implantable tissue fixation device.

4. The implantable tissue fixation device of claim 1, wherein the graft retention loop is operably connected to the at least one flexible connecting member.

5. The tissue fixation device of claim 1, wherein the at least one flexible connecting member comprises a plurality of elongate connecting filament segments extending between the first and second elongate support members.

6. The tissue fixation device of claim 5, wherein the plurality of elongate connecting filament segments are formed from a single filament.

7. The tissue fixation device of claim 5, wherein the plurality of elongate connecting filament segments comprise suture or wire.

8. The tissue fixation device of claim 5, wherein the plurality of elongate connecting filament segments are formed from a plurality of filaments.

9. The tissue fixation device of claim 5, wherein the rigid support members each include a plurality of retaining elements used to couple the plurality of elongate connecting filament segments to the rigid support members.

10. The tissue fixation device of claim 9, wherein the plurality of retaining elements comprise longitudinally spaced openings formed in the rigid support members.

11. An implantable tissue fixation device, comprising:
a graft retention anchoring portion including a plurality of non-collinear elongate members configured to be passed through a bone hole in a delivery configuration in which at least one dimension of the graft retention anchoring portion is smaller than the bone hole, the graft retention anchoring portion being further configured to be deployed on one side of the bone hole in a deployed configuration in which the at least one dimension is larger than the bone hole; and
at least one graft retention loop operably connected to a portion of the graft retention anchoring portion at a first end thereof, the at least one graft retention loop having a second end configured to operably couple to a tissue graft,
wherein the plurality of non-collinear elongate members are substantially parallel in each of the delivery configuration and the deployed configuration.

12. The implantable tissue fixation device of claim 11, wherein the graft retention anchoring portion comprises first and second elongate support members and at least one flexible connecting member operably connected to the first and second elongate support members.

13. The implantable tissue fixation device of claim 12, wherein the at least one flexible connecting member comprises a fabric.

14. The implantable tissue fixation device of claim 12, wherein the at least one flexible connecting member comprises at least one of a wire and a suture.

15. The implantable tissue fixation device of claim 12, wherein the at least one graft retention loop is operably connected to the at least one flexible connecting member.

16. The implantable tissue fixation device of claim 12, wherein the at least one graft retention loop is operably coupled to at least one of the first and second elongate support members.

* * * * *